ус005736510А

United States Patent [19]

Cornell et al.

[11] Patent Number: 5,736,510
[45] Date of Patent: Apr. 7, 1998

[54] ANTIBIOTICS 10381V, W, X,Y, Z1, Z2, PRE-B AND T

[75] Inventors: Charles Peter Cornell; Stephen Howard Grode, both of Portage; Heinz F. Meyer, Kalamazoo, all of Mich.

[73] Assignee: Pharmacia & Upjohn Company, Kalamazoo, Mich.

[21] Appl. No.: 615,209

[22] PCT Filed: Sep. 6, 1994

[86] PCT No.: PCT/US94/09647

§ 371 Date: Mar. 7, 1996

§ 102(e) Date: Mar. 7, 1996

[87] PCT Pub. No.: WO95/07292

PCT Pub. Date: Mar. 16, 1995

Related U.S. Application Data

[63] Continuation-in-part of Ser. No. 119,434, Sep. 10, 1993, abandoned.

[51] Int. Cl.$^6$ .................. A61K 37/02; A61K 35/74; C07K 7/54; C12P 21/00
[52] U.S. Cl. .................. 514/9; 514/11; 530/317; 530/323; 424/117; 424/118; 426/635; 435/71.3; 435/170; 435/822
[58] Field of Search .................. 514/9; 530/317

[56] References Cited

U.S. PATENT DOCUMENTS 5,229,362  7/1993  Kirst et al. .................. 514/9

FOREIGN PATENT DOCUMENTS

86/05785  10/1986  WIPO .
88/00200  1/1988  WIPO .

OTHER PUBLICATIONS

A.D. Argoudelis et al., The Journal of Antibiotics, XL (6):750–760, Jun. 1987.

DeBono et al.; The Structures of A10255B,–G, and J:New Thiopeptide Antibiotics Produced By *Streptomyces gardner*; The Journal of Organic Chemistry; 57(19) Sep. 11, 1992 5200–5208.

*Primary Examiner*—Cecilia J. Tsang
*Assistant Examiner*—Jennifer Harle
*Attorney, Agent, or Firm*—Martha A. Gammill

[57] ABSTRACT

Antibiotics 10381v, w, x, y, z1, z2, pre-b and t are antibiotics producible by culturing the microorganism *Streptomyces arginensis* in an aqueous medium and isolation thereof. The structure of Antibiotic 10381y is given below as formula IV. These antibiotics inhibit the growth of selected species of bacteria and may also be useful as a growth promotant in animals.

12 Claims, No Drawings

ANTIBIOTICS 10381V, W, X,Y, Z1, Z2, PRE-B AND T

This application is a 371 of PCT/US94/09647 filed Sep. 6, 1994, which is a cip of U.S. application Ser. No. 08/119,434, filed Sep. 10, 1993, now abandoned.

FIELD OF THE INVENTION

This invention relates to antibiotics designated as 10381v, w, x, y, z1, z2, pre-b and t, which are isolated from crude extracts of fermentation beers of the microorganism, *Streptomyces arginensis*.

BACKGROUND

The isolation, purification, physicochemical and biological properties of three sulfur-containing peptidic antibiotics, sulfomycin I, II and III, are disclosed in J. Antibiotics, 22(1): 12–22 (1969). Tetrahedron Lett., 29(12): 1401–4 (1988), discloses the structure of sulfomycin I, a modified peptide antibiotic. A revised structure of the structurally related antibiotic, berninamycin A, was also proposed. Tetrahedron Lett., (31): 2791–4 (1978), discloses methanolysis products of sulfomycin I. Tetrahedron Lett., (9): 735–6 (1977), discloses acid hydrolysis products of sulfomycin I.

Chemical Abstracts 73(1): 2666c (Japanese Patent 45006880) discloses the preparation of sulfomycin I by the cultivation of *Streptomyces viridochromogenes var sulfomycini*. U.S. Pat. No. 4,007,090 discloses and claims a novel fermentation process for the preparation of sulfomycin I from the microorganism *Streptomyces cineroviridis*. Chemical Abstracts 73(17): 86558e (Japanese Patent 45017588) discloses the preparation of Sulfomycins II and III by the cultivation of *Streptomyces viridochromogenes var sulfomycini*. Their uv and antibiotic spectra were similar to those of sulfomycin I.

J. Antibiotics, 45(11): 1809–1811 (1992), and European patent application 0 274 873, published 20 Jul. 1988, disclose A10255, a thiopeptide antibiotic complex, which contains a cyclic peptide core with an amino acid side chain. J. Antibiotics, 42(10): 1465–9 (1089), discloses the isolation and characterization of thioxamycin, a peptide antibiotic.

INFORMATION DISCLOSURE

The production and properties of the 10381b antibiotic complex are described in International Publication Number WO 88/00200, dated 14 Jan. 1988. According to this publication, the 10381b antibiotic complex is produced by fermentation of a nutrient medium with the microorganism *Streptomyces arginensis*. Furthermore, this publication stated that the 10381b complex comprises a group of at least five antibacterial agents active mainly against Gram-positive organisms and having physical properties similar to those reported for the sulfomycin group of antibiotics. The main components of the 10381b complex were designated $10381b_2$ and $10381b_3$. Of these two components, $10381b_2$ was isolated in sufficient quantity and purity to permit biological and chemical characterization. The structure of $10381b_2$ was thought to be identical to the peptide antibiotic sulfomycin I from *Streptomyces viridochromogenes;* this has since been confirmed. The 10381b antibiotic complex displays antimicrobial activity against Gram-positive bacteria and is useful as a growth, promotant for meat-producing animals, such as poultry, swine and cattle. However, this publication does not teach or disclose the isolation or identification of other components of the 10381b antibiotic complex, especially Antibiotics 10381v, w, x, y, z1, z2, pre-b and t of the present invention.

The production and properties of arginomycin (antibiotic $10381a_1$) are described in International Publication Number WO86/05785, dated 9 Oct. 1986, and in A. D. Argoudelis et al., The Journal of Antibiotics, XL (6):750–760, June 1987.

None of the references in this field known to Applicant teaches or suggests Antibiotics 10381v, w, x, y, z1, z2, pre-b and t of the present invention.

SUMMARY OF THE INVENTION

The present invention particularly provides:

A compound of the formula I, II, III, IV, V, VI, VII, or IX or pharmacologically acceptable salts thereof;

A feed composition, which comprises animal feed and a compound of the formula I, II, III, IV, V, VI, VII or IX, or any combination thereof;

An animal premix, which comprises a compound of the formula I, II, III, IV, V, VI, VII or IX, or any combination thereof, and a suitable inert carrier therefor; and A method for promoting growth in animals which comprises administering to the animals an effective amount of a compound of the formula I, II, III, IV, V, VI, VII or IX, or any combination thereof.

The detection, isolation and identification of these antibiotics was difficult and unexpected and required skill beyond that of one of ordinary skill in the antibiotic art. In addition, there are unexpected and advantageous properties associated with these antibiotics, e.g., Antibiotic 10381y has increased antimicrobial activity when compared to that of component $10381b_2$.

Essentially pure Antibiotics 10381v, w, x, y, z1, z2, pre-b and t have been isolated from crude extracts of fermentation beers of the microorganism *Streptomyces arginensis*. The unique structures of these compounds are also provided. Antibiotic 10381y has been found to have higher bioactivity than other components within the 10381b antibiotic complex, as described more fully below.

The antibiotics of the present invention are produced by a naturally occurring microorganism, *Streptomyces arginensis*. As such, these antibiotics may be produced by this microorganism as it exists in its natural state. The present invention as it is directed to these antibiotics do not encompass any composition thereof as might have or does exist or occur in nature. Rather, the present invention provides for the production and isolation of these antibiotics in a manner rendering it practically useful, e.g., for pharmacological and other antimicrobial purposes and for veterinary uses.

In the text that follows where reference is made to the "10381b component," it is understood that this component is the same as and is more precisely identified as the known $10381b_2$ component.

Antibiotics 10381v, w, x, y, z1, z2, pre-b and t are obtainable from the cultivation of *S. arginensis*. The description of the taxonomy and growth of this microorganism is incorporated by reference herein from International Publication Number WO 88/00200, published 14 Jan. 1988. The description of the fermentation and recovery of the 10381b antibiotic complex is also incorporated by reference herein from this publication. Preferred procedures for the preparation of the 10381b antibiotic complex are described in Preparations 1 and 2 below, with Preparation 2 being most preferred.

A group of mutants, each with increased titer compared to the parent strain, *Streptomyces arginensis* may be used for the preparation of the components of the 10381b complex.

The new strains are made using standard mutagenesis and selection techniques. These include chemical mutagenesis with N-methyl-N'-nitrosoguanidine (Delic et al. (1970), Mutat. Res. 9:167), Nitrous acid (Crueger and Crueger (1984), Biotechnology: A Textbook of Industrial Microbiology, p. 16, Sinauer Associates, Inc., Sunderland, Mass., USA) and irradiation with ultraviolet light (Thrum (1984) in Biotechnology of Industrial Antibiotics (Vandamme, ed.), Marcel Dekker, New York, pp. 373–374. Selection techniques include simple reisolation of the strain by the selection of an isolated colony, selection of specific colony morphologies, and selection for resistance to analogues of components thought to be in the biosynthetic pathway of the product, the 10381b complex (Crueger and Crueger (1984), Biotechnology: A Textbook of Industrial Microbiology, pp. 24–25, Sinauer Associates, Inc., Sunderland, Mass., USA). These strains are utilized because they produce more of the 10381b complex. This means that less volume of culture needs to be grown to obtain material to isolate the components. The mutagenesis and selection do not significantly alter the component ratios in the 10381b complex.

The isolation of these antibiotics from crudes of the 10381b antibiotic complex (which contains the known 10381b component and the components, which were identified as part of the present invention) is accomplished by chromatographic separation on reversed phase-HPLC columns. The preferred starting materials are second crop crudes of the 10381b antibiotic complex, because the components of the present invention are enriched in these second crops. Also, another way of obtaining a fraction enriched with the components of the present invention is to perform a second extraction of an already extracted beer. The preferred column is a Zorbax C8, 5 μm, with a mobile phase of water-tetrahydrofuran (THF)-acetonitrile (ACN) (60:27:3); other columns, e.g., Waters DeltaPak C18, may also be used but give poorer separation. The mobile phase may be modified to obtain different retention times (influencing also the separation). Preferred procedures for the preparation of the 10381b components are described in Example 6 below.

In general, the antibiotics of the present invention, including large amounts of purer Antibiotic 10381y, may be prepared by repeated chromatography on a Waters DeltaPak C18 cartridge (50×300 mm) with water-THF-ACN (60:27:3) as mobile phase as follows: A Waters DeltaPrep 3000 is used to process about 5.2 g of crude 10381b antibiotic complex in 164 chromatographies of about 32 mg each. Eluate pools of components 10381b, 10381x, etc. are formed and worked up to products of different purities. The first 10381y pools are concentrated to 80–150 ml and rechromatographed on the same cartridge with an identical mobile phase; in a variation of this procedure, a final pool of approximately 2 liters of 10381y eluates is concentrated to about 600 ml aqueous concentrate; this is extracted with 60 ml of methylene chloride; the extract is evaporated and the residue dissolved in mobile phase for the second chromatography. This variation of the procedure (for the final pool of 10381y eluates) results in a smaller feed volume and subsequent better chromatographic separation from which 18 mg of chromatographically pure 10381y may be obtained by concentrating the 10381y pool to an aqueous, extracting that with 0.1 volumes of methylene chloride, concentrating the extract to a slurry of about 1 ml and completing the crystallization by the addition of 3 ml n-heptane. For more details of this procedure, please see Example 2 below.

The purest Antibiotic 10381y may be prepared by double chromatography on Zorbax 5C8 with the water-tetrahydrofuran-acetonitrile mobile phase as described more fully in Example 3 below. Also in Tables IA and IB below, the analytical HPLC retention times for the antibiotics of the present invention, 10381v, w, x, y, z1, z2, pre-b and t, are given.

The structures of the antibiotics of the present invention were determined by NMR spectroscopy and mass spectrometry. For example, the application and analysis of such experiments led to the identification of Antibiotic 10381y as component 10381b$_2$ of International Publication Number WO 88/00200, minus the two terminal dehydroalanine residues. Therefore, in the Formula Chart below, Antibiotic 10381y has been identified as the compound of formula IV and component 10381b$_2$ has been identified as the compound of formula VIII (which is the same as sulfomycin I).

Also in the Formula Chart below, the compound of formula I is Antibiotic 10381v; the compound of formula II is Antibiotic 10381w; the compound of formula III is Antibiotic 10381x; the compound of formula IV is Antibiotic 10381y, as noted above; the compound of formula V is Antibiotic 10381z1; the compound of formula VI is Antibiotic 10381z2; the compound of formula VII is Antibiotic 10381pre-b; and the compound of formula IX is Antibiotic t.

It will be apparent to those skilled in the art that these antibiotics of formulas I–VII and IX contain several asymmetric carbons. All of the enantiomorphic and stereoisomeric forms of these compounds are included within the scope of the present invention.

The present invention also provides for pharmacologically acceptable salts of the compounds of formulas I–VII and IX. Pharmacologically acceptable salts refers to those salts which would be readily apparent to a pharmaceutical chemist to be equivalent to the parent compound in properties such as formulation, stability, patient acceptance and bioavailability.

All of the compounds of the present invention are useful as antibiotics and as such may be useful for treating certain bacterial infections and/or for preventing or reducing the growth of certain microorganisms in various environments. For example, the bioactivity of Antibiotic 10381y was found to be about double that of the 10381b antibiotic complex or the 10381b component against a variety of microorganisms. In Table III below, the bioactivities of the three major 10381b complex components (b, x and y) were compared to that of the 10381b complex using the in vitro Minimal Inhibitory Concentration assay, described in Example 5 below. This assay measures the ability of a compound to inhibit the growth of certain types of anaerobic bacteria which normally inhabit the gut of poultry, swine or cattle. From Table III, it is clear that the "Y peak" or Antibiotic 10381y is consistently more active (lower MIC concentrations) than the individual b and x peak materials or the 10381b complex, especially against the Clostridial and Streptococcal species, which have been reported to be involved with growth suppression in chickens and swine, while it retains low activity against rumen anaerobes such as M. elsdenii and S. ruminantium (which are necessary components of the microflora of ruminants), thus suggesting its utility as a growth promotant in ruminants, such as cattle, in addition to its growth promotion activity in monogastrics, such as poultry or swine.

Table IV below gives additional bioactivity data for some of the 10381b components and for the complex. The bioactivity data were obtained using the in vitro Minimal Inhibitory Concentration assay that is described in Example 5 below. The bioactivity data for components x, b, and y found in the study described in Table IV differ slightly from the equivalent results from the study described in Table III. Such differences are commonly seen when comparing results between separate runs of in vitro antibacterial assays, especially when different lots of antibiotics are tested. Outside of these differences (and the inconsistent result obtained for the x component against strain P1083C1), the results between the two assays are consistent and indicate that, at least in vitro, component y is the most active, with component b being the second most active of the individual components. Components pre-b, v and w, like component x, are considerably less active.

The antibiotics of the present invention are also useful to promote growth in ruminants, such as cattle and sheep, and in nonruminant, monogastrics, such as poultry (e.g., broiler chicks and turkeys) and swine. The dosages and modes of administration for the use of the antibiotics of the present invention to promote growth in animals, such as poultry, swine and cattle, world be readily ascertainable to one of ordinary skill in the veterinary art. Typically, an antibiotic of the present invention for growth promotion would be administered to animals in their feed.

For example, preferably, Antibiotic 10381y may be prepared in the form of a powder or granule contained in a premix having a suitable inert carrier, such as soybean meal, rice hulls or limestone, which would then be blended into the feed of the animal. For broiler chicks, the amount of Antibiotics 10381y effective to promote growth in chicks is from about 0.5 to about 11 mg/kg of feed, preferably about 1 to about 2 mg/kg of feed, and most preferably about 1 to about 1.5 mg/kg of feed. For swine, the amount of Antibiotic 10381y effective to promote growth in swine is from about 1 to about 55 mg/kg of feed, preferably about 2 to about 6 mg/kg of feed, most preferably about 2 to about 3 mg/kg of feed.

DESCRIPTION OF THE PREFERRED EMBODIMENTS

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

Isolation of 1031B Antibiotic Complex

The whole beer from an *S. arginensis* fermentation is adjusted to a pH of 10 with sodium hydroxide. The beer is then extracted with 2×0.5 volumes of ethyl acetate and assayed (HPLC) to confirm that the extraction is complete. The combined extracts are concentrated (rotary still, vacuum, 40° C. water bath) to 0.4 beer volumes (part of the 10381b complex may precipitate). Slowly, while stirring, 1 volume of heptane is added and the mixture is allowed to settle for a few minutes. It is checked with a drop of heptane as to whether the precipitation is completed. Some more heptane may be added to the slurry, if needed. The mixture is cooled to 4° C. and the precipitate is isolated by filtration or centrifugation. It is washed with heptane, dried (40° C./vacuum) to a constant weight and assayed by HPLC.

PREPARATION 2

Isolation of 10381B Antibiotic Complex (Refer to Chart A)

The whole beer from an *S. arginensis* fermentation is extracted with 1 volume of ethyl acetate at harvest pH (approximately 7.5). The resulting ethyl acetate extract is concentrated to 30 g/l. Two volumes of heptane are added to the concentrate and it is cooled to -20° C. for two hours. It is then centrifuged, decanted, washed with heptane, and again centrifuged and decanted, and finally dried to obtain crude 10381b complex.

EXAMPLE 1

Preparation of Antibiotic 10381Y (Small Quantities)

A small amount of impure 10381y may be prepared by chromatography on Zorbax 5C8 with water-acetonitrile (ACN) (55:45) as mobile phase as follows:

20 mg of a crude 10381b complex, prepared by procedures analogous to those described in Preparations 1 and 2 above, (with 85% 10381b component, as measured by HPLC, and an unknown amount of 10381y component) is dissolved in 1.0 ml mobile phase, water-acetonitrile (ACN) (55:45); 100-µl injections of this solution are chromatographed on a 21×250-mm Zorbax 5C8 column with 8 ml/min of mobile phase; the eluates containing the 10381y peak (RT=17 min) are collected and combined. This pool is frozen; the organic solution decanted from the ice and evaporated; the residue is crystallized from 100 µl of methanol and 300 µl of dimethyl ether by the addition of 800 µl of n-heptane.

Following this procedure, 1.5 mg 10381y of 57% purity was obtained.

EXAMPLE 2

Isolation of 10381X, 10381Y (Larger Quantities), 10381B and Other Minor 10381 Components A. Preparation of the Delta Prep 3000

The preparative chromatographies are carried out on a Waters Delta Prep 3000 preparative chromatography system. One Waters Delta-Pak C18 radial compression cartridge (50×300 mm, 15 µm-particles with 100 Å pore size) is used. The Delta Prep 3000 system is configured such that the eluate stream passes through a Pharmacia LKB Bromma model 2238 UVICORD SII UV detector (at absorbance of 254 nm) interfaced to both a Pharmacia LKB Bromma model 2210, 2 channel strip chart recorder, and a Waters MAXIMA 820 electronic chromatography dam collection system. The chromatography is performed with 600 psi radial compression on the column and a flow rate of 35 ml/min. These conditions result in approximately 350 psi back pressure on the system during the chromatographies.

B. Preparation of the Column Feed Material

The feed material is prepared by dissolving 500 mg of crude 10381b complex, prepared by procedures analogous to those described in Preparations 1 and 2 above, in 31.25 ml of a mixture of acetonitrile (ACN)-milli-Q water (water)-dimethylformamide (DMF)(25:5:1.25). A vortex mixer and sonication are used to aid dissolution. The solution is stored at 4° C. overnight, during which time a dark material precipitates. The mix is centrifuged for 15 minutes at 5000 rpm in a Beckman model J2-21 centrifuge. The solids pellet is analyzed by HPLC and found to contain <1 mg 10381b component. The clear feed solution is decanted and stored at 4° C. until required for the chromatography. The solids content of this clear solution is determined by evaporating 1 ml of the solution in a tared aluminum dish with a gentle stream of nitrogen, while applying heat to the dish via a steam-heated hot plate until the solvent has evaporated, then placing the dish in a steam-heated vacuum tower for ten minutes. The dish is then re-weighed.

In the present experiment, the solids were determined to be 16 mg/ml.

C. Preparation of the Mobile Phase

A mobile phase consisting of water-ACN-tetrahydrofuran (THF) in a ratio of 60:3:27 may be used. However, the composition of the mobile phase may also be in a ratio of 68:3.3:28.7 or any similar ratio. Using the first ratio, a sample is loaded for 1 minute at a flow rate of 10 ml/min, followed by elution with a flow rate of 35 ml/min for 50 minutes. Using the second ratio, the column is eluted for a total of 60 to 70 minutes, as needed to complete the chromatography of the b component.

In addition to the water-ACN-THF mobile phase, a mobile phase containing ammonium acetate-ACN also may be utilized. However, this mobile phase was found to be less effective.

Anticipating the high cost of UV grade tetrahydrofuran (THF) at a larger scale, "non-spectro" THF (Burdick & Jackson) is used in the mobile phase. The other components are as originally stated. The HPLC trace of this run leads to the conclusion that there is no appreciable difference between the UV grade and non-spectro grade THF for the purposes of this experiment, and that the non-spectro grade THF does not interfere with the absorbance at 254 nm of the 10381b components. Previous experiments have revealed that non-spectro ACN likewise does not interfere with UV absorbance above 220 nm.

D. Sample Collection and Pool Formation

The column effluent stream is collected in 30-second fractions on a Pharmacia LKB Bromma model 2211 Super-Rac fraction collector. Using the strip chart recording as a guide, pools are formed of the v-, w-, x-, y-, z1, z2 and pre-b component fractions.

1) Processing of Components 10381x and 10381b

Components 10381x and 10381b are collected and pooled separately until 4 liters of each are available. Each pool is then subjected to rotary evaporation on a Buchi model RE-121 rotavapor at 40° C. bath temperature and vacuum of ~40 Torr to remove the organic phase. The condenser unit of the rotavapor is chilled by an Endocal RTE-5B refrigerated circulating bath at 4° C. Each pool is concentrated to approximately ⅕ volume, during which concentration a precipitate is formed. The concentrates are then stored at 4° C. overnight. The following day each concentrate is centrifuged 20 minutes at 5000 rpm in a Beckman J2-21 refrigerated centrifuge with a JA-10 head. The supernate is decanted into a separate pool. The precipitate pellet is reslurried in a small amount (several ml) of supernate, then transferred to a 50-ml sterile disposable centrifuge tube. Each time a 4-liter elute pool is obtained, it is processed as described and added to the precipitate pellet. When the tube is approximately ½ full, it is centrifuged 20 minutes at 5000 rpm in a Beckman J2-21 refrigerated centrifuge with a JA-14 head and 50-ml adapter cups. The supernate is decanted and added to the original supernate pools. The precipitate pellet is washed with several ml of milli-Q water (enough to slurry the pellet), then centrifuged again for 20 minutes at 5000 rpm, and the supernate decanted and added to the supernate pool as before. The washed precipitate pellet is dried on a Virtis Unitrap II lyophilizer.

In the present experiment, the supernates were assayed by HPLC and found to contain only small amounts of components 10381b and 10381x, less pure than the precipitated products. They were therefore discarded.

2) Processing of the "y" Peak Pool

The y-peak fractions are pooled to 2 liters, subjected to rotary evaporation, as described above, for the x- and b-pools, then rechromatographed. The volume of y-concentrate loaded onto the Delta Prep may vary from run to run, but is generally from 80 to 150 ml, dependent upon the total amount of material available. Fractions are collected as above, and the fractions containing x- and b-components are added back to their respective pools. The fractions containing purified y-component are pooled, concentrated to an aqueous in a rotary still at 40° C. bath temperature and 40 Torr vacuum, and extracted with 2×0.1 volumes of methylene chloride. The extracts are pooled according to purity (HPLC), concentrated, transferred to a 20-ml vial, evaporated, and crystallized from a minimum of acetone with 3 volumes of heptane. The slurry is centrifuged, the supernate decanted, the crystals washed with heptane and dried at approximately 40 Torr/30° C.

For the last 2-liter pool of once chromatographed component 10381y, an improved process may be used as follows: The pool is concentrated to an aqueous and extracted twice with 0.1 volume of methylene chloride; the extracts are combined, concentrated to a small volume, transferred to a tared 20-ml scintillation vial and blown dry with filtered nitrogen at room temperature. The dried material is redissolved in 5 ml of the mobile phase, water-ACN-THF (68:3.3:28.7), for the second chromatography. The y-peak fractions are pooled and worked up as above.

97% pure 10381y was obtained in the present experiment.

For the assays of starting material eluates and purification of 10381y, a Whatman 5-C8 column may be used with 0.01M pH 5.5 sodium phosphate-ACN (55:45) at 1 ml/min, detection at 248 nm. However, a Nucleosil 5-C18 column with a mobile phase of 0.01M pH 5.5 sodium phosphate-ACN-THF (60:3:27) at 1 ml/min, detection at 248 nm allows for a better separation of component 10381b from component 10381y.

E. Conclusions

For the present experiment, the Delta Prep 3000 was used to process about 5.2 g of crude 10381b antibiotic complex in 180 runs, including 16 second chromatographies for 10381y, resulting in a total production of the following components: approximately 1484 mg of 10381b, approximately 379 mg of 10381x and approximately 50 mg of 10381y.

EXAMPLE 3

Preparation of Antibiotic 10381Y (Pure Form)

The purest 10381y may be prepared by double chromatography on Zorbax 5C8 with the water-tetrahydrofuran-acetonitrile mobile phase as follows:

A 21×250 ml Zorbax 5C8 column is equilibrated with the water-tetrahydrofuran-acetonitrile mobile phase; 200 µl of a 100 mg/ml dimethylformamide (DMF) solution of crude 10381b complex, containing 9.5% of 10381y, and prepared by procedures analogous to those described in Preparations 1 and 2 above, is injected and developed at 8 ml/min; eluate with 10381y is collected; and the column is washed for 15 min with 80% aqueous acetonitrile before the next injection of feed (overnight the column is stored in this solvent also). The 10381y eluates from a series of separations are pooled, concentrated to an aqueous and extracted with methylene chloride; the extract is evaporated, and the residue redissolved in dimethylformamide for the second chromatography. The 10381y-eluate is again concentrated and extracted with methylene chloride; the extract is concentrated to a slurry and the crystallization is completed by the addition of n-heptane. Small quantities (that are difficult to isolate in this way) are alternately isolated by evaporating the extraction solvent and freeze drying the residue from a t-butanol solution.

In the present experiment, 6.5 mg of chromatographically pure 10381y was obtained from 300 mg of crude 10381b complex.

The analytical HPLC retention times (which were obtained by using a 4.6×250 mm Zorbax 5C8 column with 1 ml/min water-THF-ACN (60:27:3)) for the 10381 components of the present invention are given in Table IA below.

EXAMPLE 4

Determination of the Structure of Antibiotic 10381Y (Formula IV) and Other 10381 Antibiotics The structure of Antibiotic 10381y was determined by NMR spectroscopy and mass spectrometry. The standard method of identification by NMR is to correlate all H—H connectivities by Correlation Spectroscopy (COSY) and transfer that information to the carbon skeleton by means of a Heteronuclear Correlation Spectroscopy (HETCOR) experiment. Difficulties arise in highly unsaturated molecules (such as 10381y) because the large number of non-protonated carbons represent breaks in the sequence. In these cases, less sensitive interactions such as Nuclear Overhauser Enhancement (NOE) and long-range C—H correlations are used to bridge the many isolated spin systems. The application and analysis of such experiments led to the identification of Antibiotic 10381y as 10381b minus the two terminal dehydroalanine residues.

Therefore, Antibiotic 10381y has been identified as the compound of formula IV, which is 52-de[1-[[[1-(aminocarbonyl)ethenyl]amino]carbonyl]ethenyl]-sulfomycin I, in the Formula Chart below. The complete assignment of all $^1$H and $^{13}$C resonances in the molecule is presented in Table II below.

Using analogous procedures, the $^1$H resonances of the other components were found to be as follows:

Antibiotic 10381v of formula I: 8.14, 8.46, 8.29/7.84, 8.81, 9.86, 5.60/5.65, 6.41/5.73, 9.15, 9.89, 6.51, 1.78, 2.58, 8.43, 6.43, 8.50, 3.29, 9.40, 6.25, 4.48, 1.21, 5.36, 2.55, 4.37, 8.10, 4.16, 1.10, 5.18, 8.47.

Antibiotic 10381pre-b of formula VII: 7.49/7.91, 5.63/6.10, 9.10, 5.71/5.71, 10.03, 6.52/5.94, 10.48, 8.24, 8.48, 8.64, 9.97, 5.57/5.53, 6.49/5.76, 9.21, 9.71, 6.57, 1.76, 2.62, 8.21, 4.73–4.84, 8.75, 9.50, 6.27, 4.49–4.58, 1.20, 4.95, 2.54, 4.49–4.58, 8.10, 4.18–4.27, 1.13, 5.23, 8.42.

Antibiotic 10381z2 of formula VI: 7.50/7.91, 5.64/6.10, 9.09, 5.72/5.72, 10.04, 6.53/5.94, 10.48, 8.24, 8.47, 8.66, 9.88, 5.62/5.53, 6.49/5.73, 9.22, 9.71, 6.56, 1.77, 2.55, 8.23, 4.76, 8.78, 9.46, 6.44, 1.77, 2.62, 4.59, 8.07, 4.25, 1.12, 5.17, 8.44.

Antibiotic 10381x of formula III: 7.50/7.91, 5.66/6.12, 9.09, 5.70/5.75, 10.12, 6.67/5.96, 10.49, 8.20, 8.56, 5.02, 8.25, 1.49, 2.59, 8.25, 5.42, 8.15, 1.60, 4.18/4.57, 8.85, 2.53, 4.37, 8.03, 2.17, 1.04, 1.05, 8.37.

Antibiotic 10381w of formula II: 7.67/8.15, 5.81/6.57, 10.69, 8.20, 8.53, 5.01, 8.24, 1.48, 2.66, 8.24, 5.43, 8.16, 1.60, 4.18/4.56, 8.70, 2.53, 4.37, 8.04, 2.17, 1.00, 1.00, 8.38.

Antibiotic 10381t of formula IX: 8.01/7.82, 8.49, 8.13, 2.53, 5.02, 1.49, 8.19, 8.23, 5.43, 1.60, 8.15, 2.53, 4.55/4.20, 8.86, 4.38, 2.18, 0.96, 0.96, 7.90, 8.36.

Mass spectral data was acquired using electrospray ionization and revealed an ion at m/e 1130.0 for 10381y which corresponded to the M+Na$^+$ adduct. The average mass was therefore determined to be 1107.0 amu which was consistent with a molecule of formula $C_{48}H_{46}O_{14}N_{14}S_2$ (calculated average molecular weight=1107.1).

Using procedures analogous to those described above, the structures and average mass of the other 10381b antibiotics of the present invention were found to be as follows: The compound of formula I is Antibiotic 10381v (1037.7 amu); the compound of formula II is Antibiotic 10381w (815.7 amu); the compound of formula III is Antibiotic 10381x (953.9 amu); the compound of formula IV is Antibiotic 10381y, as noted above; the compound of formula V is Antibiotic 10381z1 (1201.5 amu); and the compound of formula VI is Antibiotic 10381z2 (1185.7 amu); the compound of formula VII is Antibiotic 10381pre-b (1215.1 amu) and the compound of formula IX is Antibiotic 10381t (746.2 amu).

EXAMPLE 5

Minimal Inhibitory Concentration Determination of Antibiotics 10381B Components The bioactivities of the 10381b components were compared to that of the 10381b complex using the in vitro Minimal Inhibitory Concentration (MIC) assay described below. The assay measures the ability of a compound to inhibit the growth of certain types of anaerobic bacteria which normally inhabit the gut of poultry, swine or cattle.

I. Compound Preparation

Two mg/ml solutions of the drugs to be tested are made in 10% v/v ethanol/water. This stock is then diluted to one mg per ml and then further diluted through a series of ten-two fold dilutions. At each concentration an aliquot is placed in a sterile petri plate. Nine volumes of molten agar are then added to each plate, mixed and allowed to harden at room temperature. These plates are then transferred to a Coy chamber and allowed to dry and equilibrate with the oxygen free atmosphere.

II. Inoculum Preparation

Organisms used for MIC testing are inoculated into broth media, and incubated 18–24 h at 39° C. prior to use. The cultures are then diluted to equal the turbidity of a 0.5 MacFarland barium sulfate standard, except for the porcine isolates P108-3C1, P105-1C3 and P105-1C4 which are diluted 1:1. All inoculations and dilutions are performed in the anaerobic chamber using broth media and syringe transfer through the butyl robber stoppers.

Freshly prepared and diluted cultures are loaded into the wells of a Steers replicator device. This apparatus can dispense ca 10 µl of each of 32 cultures onto the surface of the preincubated agar plates. One hour after the inoculation, the inoculum will have been absorbed and the plates are inverted and incubated at 38°–39° C. for 48 h. Plates are then removed from the chamber and the MIC for the test compounds determined. MIC's are reported as the lowest concentration of a compound which prevented detectable growth of a test organism on the agar plates. For tests of compounds which failed to yield a clear cut breakpoint between growth and no growth, the MIC is considered to be one dilution higher than the concentration which yields either an indistinct haze of growth or 3–5 individual colonies within the test zone. Thus, each set of test plates yields individual MIC values for each of the 32 test organisms.

III. Conclusions

In Table III, using the above described assay, the following antibiotics were compared: 10381b complex, 10381b component, 10381x component and 10381y component.

Although the exact difference in activity between the components varies with the individual microorganism being tested, it is clear from Table III that the "Y peak" or Antibiotic 10381y is consistently more active (lower MIC concentrations) than the individual b and x components or the 10381b complex, especially against the Clostridial and Streptococcal species which have been reported to be involved with growth suppression in chickens and swine, while it retains low activity against rumen anaerobes such as *M. elsdenii* and *S. ruminantium* (which are necessary components of the microflora in ruminants), thus suggesting its utility as a growth promotant in ruminants in addition to its growth promotion activity in monogastrics, such as poultry or swine.

Table IV below gives additional bioactivity data for some of the 10381b components and for the complex, which data was obtained using the above described assay. The bioactivity data for components x, b and y found in the study described in Table IV differ slightly from the equivalent results from the study described in Table III. Such differences are commonly seen when comparing results between separate runs of in vitro antibacterial assays, especially when different lots of antibiotics are tested. Outside of these differences (and the inconsistent result obtained for the x component against the strain P1083C1), the results between the two assays are consistent and indicate that, at least in vitro, component y is the most active, with component b being the second most active of the individual components. Components pre-b, v and w, like component x, are considerably less active.

EXAMPLE 6

Isolation and Purification of 10381B Components X, Y, W, V, Pre-B, Z1, Z2, and T The 10381b complex is produced by fermentation of *Streptomyces arginensis* in a nutrient medium. Crudes are obtained by extraction with ethyl acetate followed by concentration and precipitation with heptane. The materials obtained are then chromatographed on various supports as described below:

10381x. Crude 10381b complex is chromatographed in 32-mg charges on a Waters Delta-Prep loaded with a Delta-Pak C18 column, using a mobile phase of water-ACN-THF (67:3:30) at 35 ml/min. The chromatography is monitored with a Pharmacia 2238 UVICORD SII UV detector, set at 254 nm, to cut fractions of 10381b, 10381x and other minor components. The 10381x eluates are pooled and stored at 4° C. When more than 50 mg of the compound has been collected, the pool is concentrated to an aqueous slurry and centrifuged. The supernate, containing little 10381b, is decanted, the solids pellet is transferred to a small vial and freeze dried.

Physical characteristics are as follows:

This material was found to be >90% pure by HPLC, containing trace amounts of 10381b, 10381y and unknown polar impurities. It was used for MS and NMR experiments without further purification by a second chromatography.

10381y. This compound is isolated from the same chromatographies as 10381x; however, since the 10381y eluates are less pure than those of 10381x, they are first concentrated to an aqueous and extracted with 2×0.1 volumes of methylene chloride. The extracts are combined, evaporated and redissolved in mobile phase for a second chromatography. The new eluate fractions are again pooled, concentrated to an aqueous and extracted into methylene chloride. The extracts are consecutively washed with 0.2 volumes of water, combined and evaporated. The residue (43 mg) is transferred to a scintillation vial and crystallized from 1 ml methylene chloride with 3 ml n-heptane as countersolvent. The slurry is centrifuged, the supernate removed with a pipette and the crystals washed with 1 ml heptane.

Physical characteristics are as follows:

The 35 mg of 10381y obtained were 98% pure according to an HPLC assay.

10381w. This compound is separated and purified by the double chromatography described for 10381y. The solids obtained from the second chromatography (34 mg) are less pure than the corresponding 10381y fraction, since much less 10381w than 10381y is contained in the crude complex. A larger amount of material stripped from the chromatographic column is therefore contaminating these solids, making their crystallization difficult. They are first dissolved in 1.5 ml methanol+1.5 ml acetone, filtered off a waxy material that contained only traces of 10381w (HPLC); with 2 ml n-heptane+0.1 ml toluene (to avoid forming two phases), then precipitated to yield the final product, 10381w.

Physical characteristics are as follows:

3.3 mg of 10381w were obtained in 74% purity.

10381v. This compound is isolated like 10381w by double chromatography and extraction of the appropriate eluate pool. The solids obtained after evaporating the solvent are pure enough to crystallize from 1 ml of acetone with 2 ml of n-heptane. The slurry is centrifuged, the supernate removed and the residue washed with heptane and dried.

Physical characteristics are as follows:

19 mg of 10381v of 82% purity were obtained.

10381pre-b. This compound is prepared from crude 10381 containing 18% 10381pre-b, by a single chromatography on a 21×250 mm Zorbax (7 µl) C8 column with water-ACN-THF (70:3:27) as mobile phase; 400 mg starting material is dissolved in 8 ml DMF and passed over the column in four runs at the relatively low flow rate of 8 ml/min. The 10381pre-b containing eluates are pooled (about 1.2 l), concentrated to ~300 ml aqueous and freeze dried to yield the final product, 10381pre-b.

Physical characteristics are as follows:

11.5 mg solids of 10381pre-b were obtained that were chromatographically pure.

10381z1. This compound is prepared by a single chromatography on a PrepPak C18 column. The final eluate pool with 10381z1 is concentrated to an aqueous of 500 ml containing 26 mg 10381z1 (HPLC, assuming the same response factor as 10381b). Methylene chloride extracts only trace amounts of the compound, ethyl acetate, at pH 6 and pH 9, and is only slightly better. The partially extracted aqueous is therefore freeze dried.

Physical characteristics are as follows:

23 mg of 10381z1 of 91% purity were obtained.

10381z2. This compound is isolated from 10381z2 eluates of the same chromatography that produced 10381z1. The eluate pool is concentrated to 470 ml aqueous; the resulting precipitate is isolated by centrifugation and freeze dried.

Physical characteristics are as follows:

The obtained 16 mg of 10381z2 were 80% pure.

10381t. This compound is separated from the complex and then purified by the double chromatography described for 10381y above: 30 mg charges are chromatographed on a Waters DeltaPrep loaded with a DeltaPak C18 column, using a mobile phase of water-ACN-THF (67:3:30) at 35 ml/min. Eluate fractions with 10381t are pooled, stored at 4° C. until enough eluate has been collected (approximately 1 liter with approximately 5 mg), and then concentrated to an aqueous and extracted with methylene chloride. The extracts are combined and evaporated; the residue is dissolved in DMF and chromatographed on a 21×250 mm Zorbax C8 column with a mobile phase of water-ACN-THF (70:3:27) at 8 ml/min. The eluate fractions containing chromatographically almost pure 10381t are combined and evaporated to give solid final product, 10381t.

Physical characteristics are as follows:

4 mg solids of 10381t were obtained as determined by HPLC.

The analytical HPLC retention time (which was obtained by using a 4.6×250 mm Zorbax 5C8 column with 1 ml/min water-THF-ACN (70:27:3)) for the 10381t component of the present invention is given in Table IB below.

More pure 10381t is prepared as follows: A crude 10381b complex is used as staring material. It is isolated by 1) extracting whole beer with n-butyl acetate, 2) concentrating the extract, 3) precipitating the 10381 complex with heptane, and 4) isolating the solid crude by centrifugation and drying.

This material is further dried (to constant weight) and then triturated with water (2 ml/g solids) to remove about 2% of polar impurities. This upgraded product, is used as starting material for the chromatographic separation of 10381t from 10381b and its other minor components.

A DeltaPak C18 column in a Waters DeltaPrep is equilibrated with a mobile phase (MP) of water-THF-ACN (67:3:30), charged with 32 mg batches, then 64 mg batches of the starting material and developed with mobile phase at 35 ml/min. A total of ~2 g crude 10381b are chromatographed. The 10381t containing eluate fractions are pooled and stored at 4° C. until they are worked up in two 500 ml batches.

These eluate pools are first concentrated to an aqueous in a vacuum still (~30 Torr, 45° C. water bath temperature) and then extracted into 3×0.1 volumes of methylene chloride. The extracts are pooled, assayed, and then concentrated to dryness. The obtained solids with 2.0 and 2.4 mg of 10381t (HPLC) are then combined with a previously obtained sample of similar purity. Each solid is leached with a few ml of methylene chloride ($CH_2Cl_2$) each and washed again with this solvent until no more activity can be extracted. The extracts are pooled, concentrated, transferred to a 1.5 ml tube and dried.

The obtained solids, freed from most of the material stripped from the DeltaPak column, are redissolved in 190 μl DMF for the second chromatography. This separation is done on a new 21×250 mm Zorbax 7 μm C8 column with water-THF-ACN (70:27:3) as a mobile phase. To minimize contaminating the eluates with material stripping from the column during development, first wash the column with 5 ml each of MP-DMF (1:1) and DMF. Then the starting material, ~10 mg crude 10381t, is injected and developed with MP at 8 ml/min. Other components of the present invention may be obtained in more pure form by following procedures analogous to those described above.

TABLE IA

ANALYTICAL HPLC RETENTION TIMES OF 10381B COMPONENTS

| 10381 | RT (min.) | $RT_b$* |
|---|---|---|
| v | 7.7 | 0.56 |
| w | 8.8 | 0.66 |
| x | 10.2 | 0.76 |
| y | 11.9 | 0.89 |
| pre-b | 12.6 | 0.94 |
| b | 13.3 | 1.00 |
| z1 | 14.9 | 1.11 |
| z2 | 16.9 | 1.25 |

*Retention time relative to 10381b component retention time, same HPLC system.

TABLE IB

ANALYTICAL HPLC RETENTION TIME OF 10381T COMPONENT

| 10381 | RT (min.) | $RT_b$* |
|---|---|---|
| b | 54 | 1.00 |
| t | 19 | 0.35 |

*Retention time relative to 10381b component retention time, same HPLC system.

TABLE II

NMR CHEMICAL SHIFTS OF 10381Y IN $d_6$-DMSO

| Position | $^1H$ | $^{13}C$ |
|---|---|---|
| 7b | 8.12 br s | |
| 7a | 7.61 br s | |
| 8 | | 164.9 |
| 9 | | 133.7 |
| 9'b | 5.80 s | 103.0 |
| 9'a | 6.55 s | |
| 10 | 10.56 br s | |
| 11 | | 161.1 |
| 12 | | 149.3 |
| 14 | | 146.7 |
| 15 | | 130.8 |
| 16 | 8.71 d | 140.1 |
| 17 | 8.29 d | 121.8 |
| 18 | | 138.7 |
| 20 | | 158.3 |
| 21 | 8.59 s | 140.0 |
| 22 | | 129.6 |
| 22'b | 5.68 s | 112.9 |
| 22'a | 5.80 s | |
| 23 | 9.98 br s | |
| 24 | | 162.7 |
| 25 | | 133.4 |
| 25'b | 5.78 s | 105.2 |
| 25'a | 6.40 s | |
| 26 | 9.18 br s | |
| 27 | | 159.8 |
| 28 | | 128.6[b] |
| 30 | | 156.8 |
| 31 | | 154.1[b] |
| 31' | 2.57[a] s | 11.5[b] |
| 32 | | 123.5 |
| 32'b | 1.76 d | 13.7 |
| 32'a | 6.50 q | 129.7 |
| 33 | 10.03 br s | |
| 34 | | 159.2 |
| 35 | | 148.8 |
| 37 | | 167.5 |
| 38 | 8.45 s | 127.0 |
| 39 | 6.46 d | 77.1 |

TABLE II-continued

NMR CHEMICAL SHIFTS OF 10381Y IN $d_6$-DMSO

| Position | $^1H$ | $^{13}C$ |
|---|---|---|
| 39' | 3.24 s | 55.4 |
| 40 | 8.35 br d | |
| 41 | | 161.3 |
| 42 | | 129.1[b] |
| 44 | | 156.3 |
| 45 | | 153.5[b] |
| 45' | 2.56[a] s | 11.5[b] |
| 46 | | 120.6 |
| 46'b | 4.46 sext | 62.5 |
| 46'a | 6.27 d | 136.7 |
| 46'b2 | 4.93 d | |
| 46'b1 | 1.21 d | 22.8 |
| 47 | 9.37 br s | |
| 48 | | 169.7 |
| 49 | 4.34 dd | 59.3 |
| 49' | 4.15 sext | 66.2 |
| 49'b | 5.22 d | |
| 49'a | 1.10 d | 20.2 |
| 50 | 8.17 br d | |
| 51 | | 160.6 |
| 52 | | 148.8 |
| 54 | | 162.3 |
| 55 | 8.53 s | 127.6 |

[a]Assignments interchangeable.
[b]The assignment of the 28, 31 and 31' series are interchangeable with the assignment of the 42, 45 and 45' series.

TABLE III

Bioactivity of Components 10381y, x and b (M.I.C. in µg/ml)

| Organism | Strain | Complex | 10381x | 10381b | 10381y |
|---|---|---|---|---|---|
| C. perfringens | P1083C1 | 0.4 | 1.6 | 0.4 | <0.2 |
| C. perfringens | P1051C3 | 50.0 | >100.0 | 50.0 | 12.5 |
| S. faecalis | P1051C4 | 12.5 | 50.0 | 12.5 | 1.6 |
| S. bovis | JB1 | 3.1 | 25.0 | 3.1 | 0.4 |
| C. perfringens | A83-RKP | 0.4 | 1.6 | 0.8 | 0.4 |
| C. perfringens | A83-3 | 0.8 | 6.3 | 3.1 | <0.2 |
| C. perfringens | A82-1 | 3.1 | 50.0 | 3.1 | 0.8 |
| S. faecalis | 71A01 | 50.0 | 100.0 | 25.0 | 6.3 |
| C. perfringens | 71A02 | 1.6 | 6.3 | 1.6 | <0.2 |
| C. perfringens | RF1B04 | 0.4 | 3.1 | 0.4 | <0.2 |
| S. faecalis | CCS1-03 | 6.3 | 50.0 | 12.5 | 1.6 |
| C. perfringens | CCS2-09 | 0.4 | 1.6 | 0.8 | <0.2 |
| C. perfringens | CCS1-11 | 3.1 | 50.0 | 6.3 | 0.8 |
| B. fragilis | UC9370 | 50.0 | 100.0 | 25.0 | 1.6 |
| C. perfringens | UC9452 | 1.6 | 6.3 | 3.1 | <0.2 |
| B. thetaiotaomicron | UC9014 | 25.0 | 50.0 | 12.5 | <0.2 |
| E. lentum | L-34 | NG | NG | NG | NG |
| B. fibrisolvens | 49 | 0.4 | 1.6 | 6.3 | <0.2 |
| B. fibrisolvens | D1 | 0.8 | 3.1 | 0.8 | <0.2 |
| M. elsdenii | B159 | >100.0 | >100.0 | >100.0 | >100.0 |
| L. multiparus | 40 | 1.6 | 6.3 | 1.6 | <0.2 |
| S. ruminantium | GA192 | >100.0 | >100.0 | >100.0 | >100.0 |
| S. ruminantium | GA31 | 50.0 | >100.0 | 100.0 | 25.0 |
| R. amylophilus | H18 | >100.0 | >100.0 | >100.0 | 100.0 |
| R. flavefaciens | FD1 | 0.8 | 6.3 | 1.6 | <0.2 |
| R. flavefaciens | C94 | 0.8 | 3.1 | 0.8 | 6.3 |
| E. ruminantium | GA195 | 0.8 | 3.1 | 0.4 | 6.3 |
| P. ruminicola | 118B | <0.2 | 0.2 | <0.2 | <0.2 |
| F. necrophorum | FN5052 | 100.0 | >100.0 | 100.0 | 25.0 |
| F. necrophorum | FN4070 | 100.0 | >100.0 | 50.0 | 25.0 |
| S. hyodysenteriae | B204 | NT | NT | NT | NT |
| S. hyodysenteriae | 16-4 | NT | NT | NT | NT |

Comments:
NG = No Growth,
NT = Not Tested;
all MICs are on a mass basis with no correction for purity.

TABLE IV

| Organism | Strain | complex | x | pre-b | b | y | v | w |
|---|---|---|---|---|---|---|---|---|
| C. perfringens | P1083C1 | 0.8 | 100. | 25.0 | 1.6 | 0.8 | 100 | >100 |
| C. perfringens | P1051C3 | 25.0 | >100 | >100 | 12.5 | 6.3 | 100 | >100 |
| S. faecalis | P1051C4 | 3.1 | >100 | >100 | 3.1 | 0.8 | >100 | >100 |
| S. bovis | JB1 | 1.6 | >100 | 50.0 | 0.8 | 0.8 | >100 | >100 |
| C. perfringens | A83-RKP | 0.4 | 50.0 | 1.6 | 0.8 | <0.2 | 1.6 | >100 |
| C. perfringens | A83-3 | <0.2 | 25.0 | 1.6 | <0.2 | <0.2 | 0.8 | 12.5 |
| C. perfringens | A82-1 | 12.5 | >100 | 12.5 | 12.5 | 12.5 | >100 | >100 |
| S. faecalis | 71A01 | 12.5 | >100 | >100 | 12.5 | 6.3 | >100 | >100 |
| C. perfringens | 71A02 | <0.2 | nt | nt | <0.2 | <0.2 | nt | nt |
| C. perfringens | RF1B04 | <0.2 | 50.0 | 1.6 | <0.2 | <0.2 | 0.8 | 100 |
| S. faecalis | CCS1-03 | 12.5 | >100 | >100 | 6.3 | 3.1 | >100 | >100 |
| C. perfringens | CCS2-09 | 1.6 | 100 | 50.0 | 0.8 | <0.2 | >100 | >100 |
| C. perfringens | CCS1-11 | <0.2 | nt | nt | <0.2 | <0.2 | nt | nt |
| B. fragilis | UC9370 | 25.0 | >100 | >100 | 50.0 | 50.0 | >100 | >100 |
| C. perfringens | UC9452 | 1.6 | 50.0 | 25.0 | 1.6 | 0.8 | 6.3 | >100 |
| B. thetaiotaomicron | UC9014 | 50.0 | >100 | >100 | 25.0 | 50.0 | >100 | >100 |
| E. lentum | L-34 | <0.2 | <0.2 | <0.2 | <0.2 | <0.2 | 25.0 | 25.0 |
| B. fibrisolvens | 49 | 1.6 | >100 | 50.0 | 1.6 | 0.4 | 50.0 | >100 |
| B. fibrisolvens | D1 | 0.4 | 100. | 12.5 | 0.8 | <0.2 | 25.0 | >100 |
| M. elsdenii | B159 | >100 | >100 | >100 | >100 | >100 | >100 | >100 |
| L. multiparus | 40 | 3.1 | >100 | >100 | 1.6 | 12.5 | >100 | >100 |
| S. ruminantium | GA192 | 1.6 | 6.3 | 6.3 | 1.6 | <0.2 | 100 | 12.5 |
| S. ruminantium | GA31 | nt | 6.3 | 50.0 | 0.8 | <0.2 | 25.0 | 1.6 |
| R. amylophilus | H18 | 1.6 | 25.0 | >100 | 1.6 | <0.2 | 3.1 | >100 |
| R. flavefaciens | FD1 | 0.8 | 100 | 25.0 | 1.6 | 0.4 | 25.0 | >100 |
| R. flavefaciens | C94 | 1.6 | >100 | 25.0 | 0.8 | 0.8 | 25.0 | 100 |
| E. ruminantium | GA195 | 12.5 | 100 | 12.5 | 12.5 | 0.8 | 12.5 | 25 |
| P. ruminicola | 118B | <0.2 | 12.5 | <0.2 | <0.2 | <0.2 | <0.2 | <0.2 |
| F. necrophorum | FN5052 | 100. | >100 | >100 | 100. | 50.0 | >100 | >100 |
| F. necrophorum | FN4070 | >100 | >100 | >100 | 100. | 50.0 | 100 | >100 |

TABLE IV-continued
| Organism | Strain | complex | x | pre-b | b | y | v | w |
|---|---|---|---|---|---|---|---|---|
| S. hyodysenteriae | B204 | >100 | >100 | >100 | >100 | >100 | >100 | >100 |
| S. hyodysenteriae | 16-4 | >100 | >100 | >100 | >100 | >100 | >100 | >100 |
Comments:
nt = not tested
CHART A
Whole Beer
↓
EtOAc Extract
↓
Crude 10381b Complex
FORMULA CHART
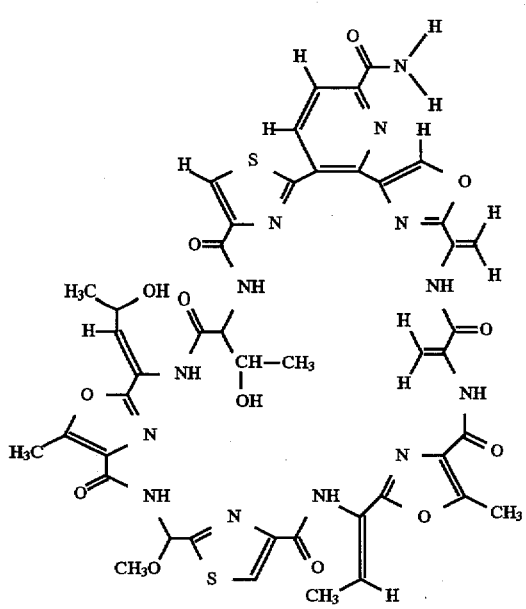
I
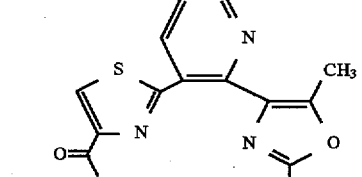
II
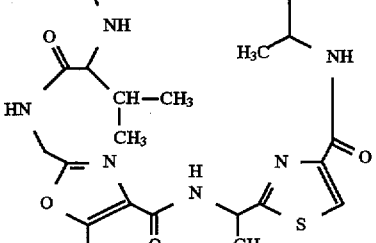
III

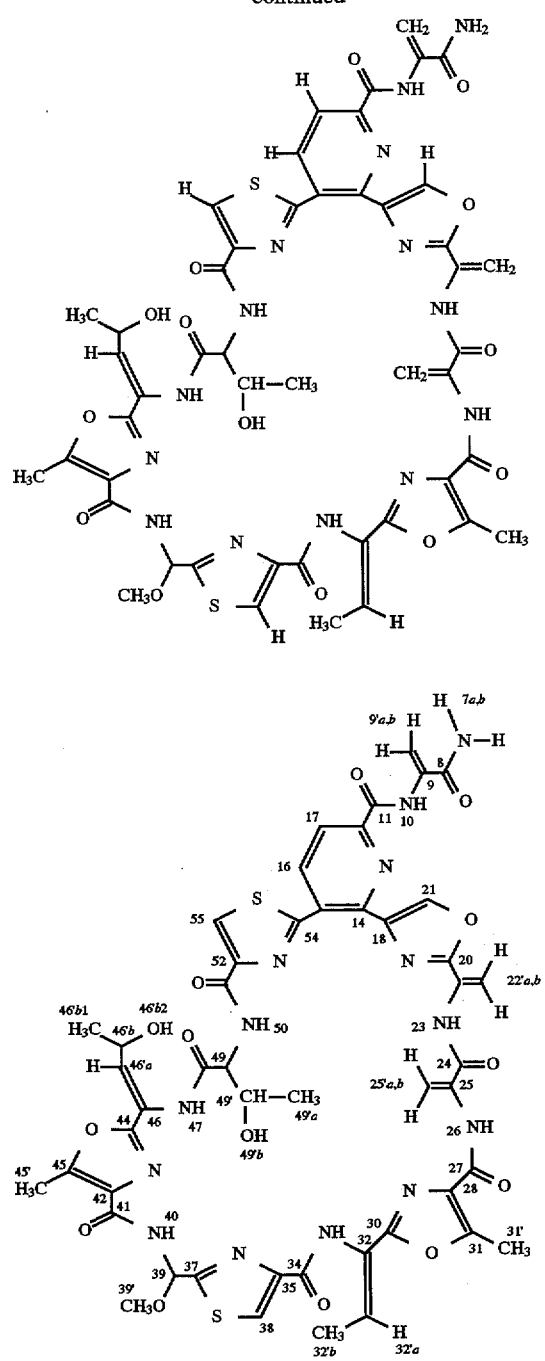
IV
IVA
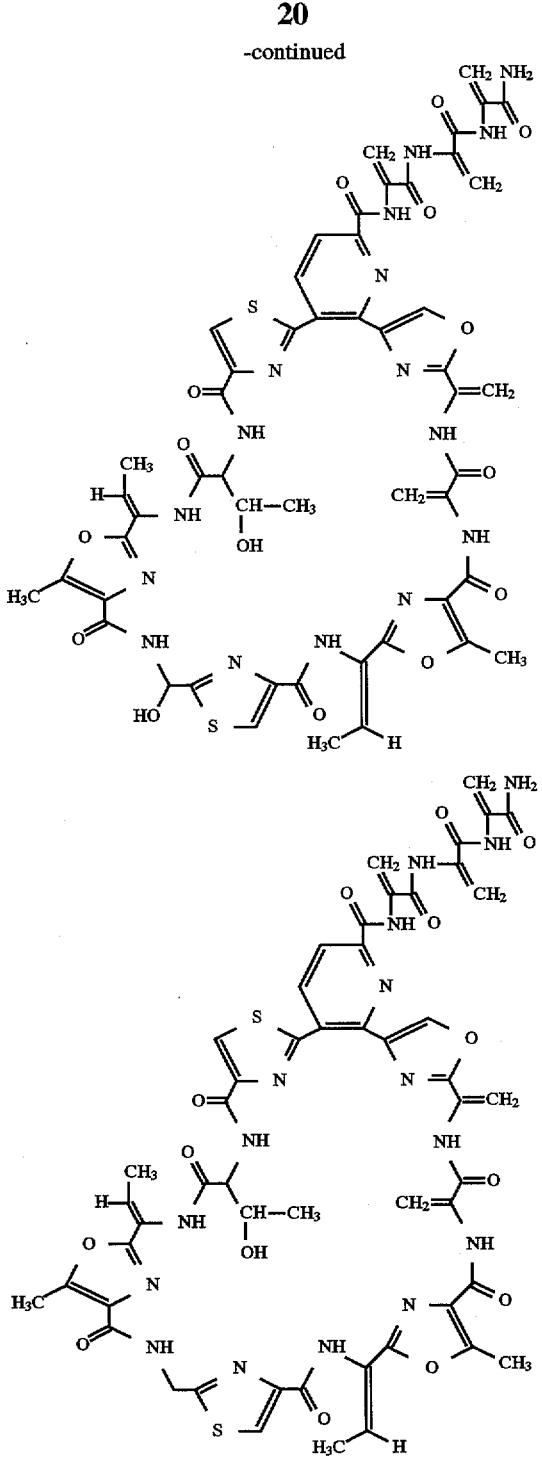
V
VI

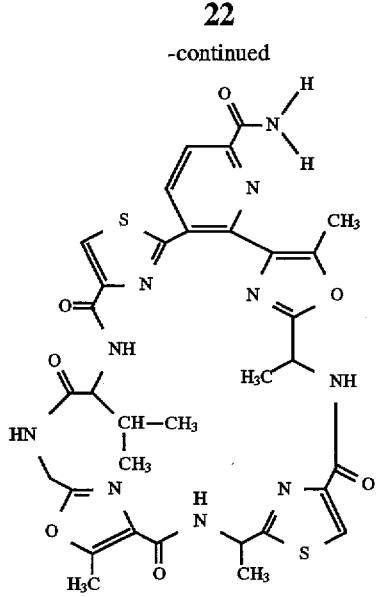
VII
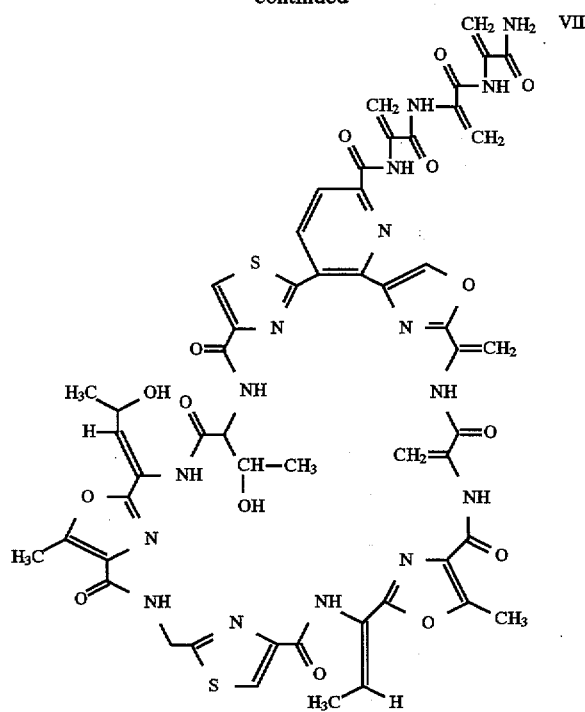
VIII
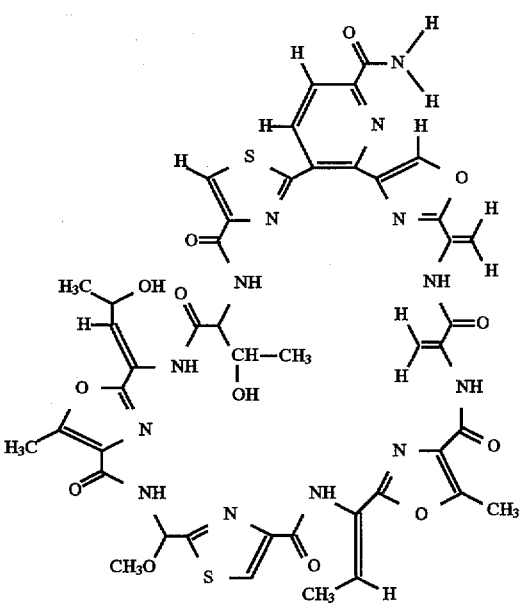
IX
We claim:
1. An isolated and purified compound of the formula I, II, III, IV, V, VI, VII, or IX:
I

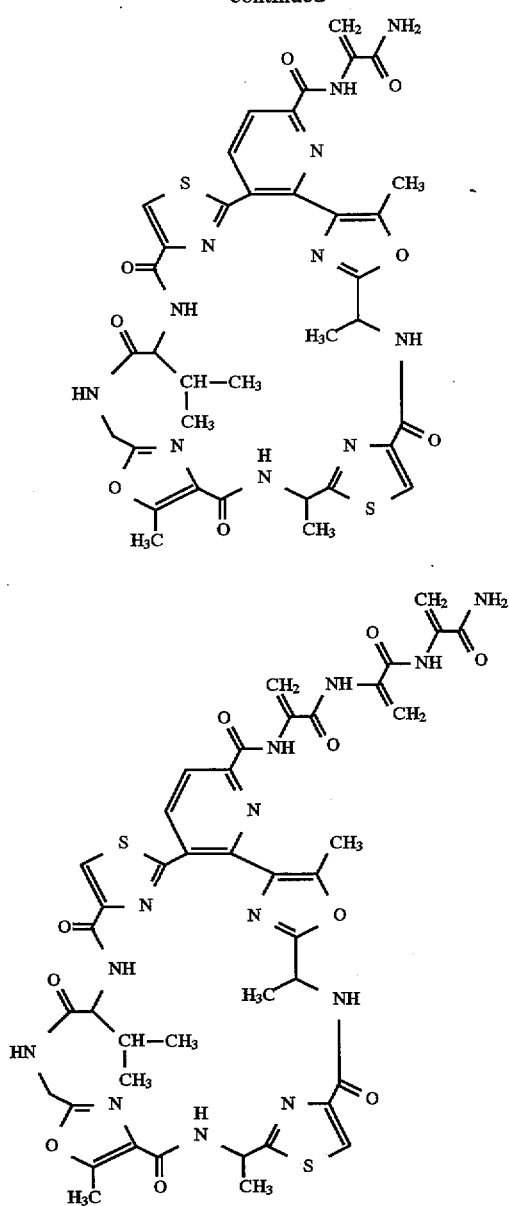
II
III
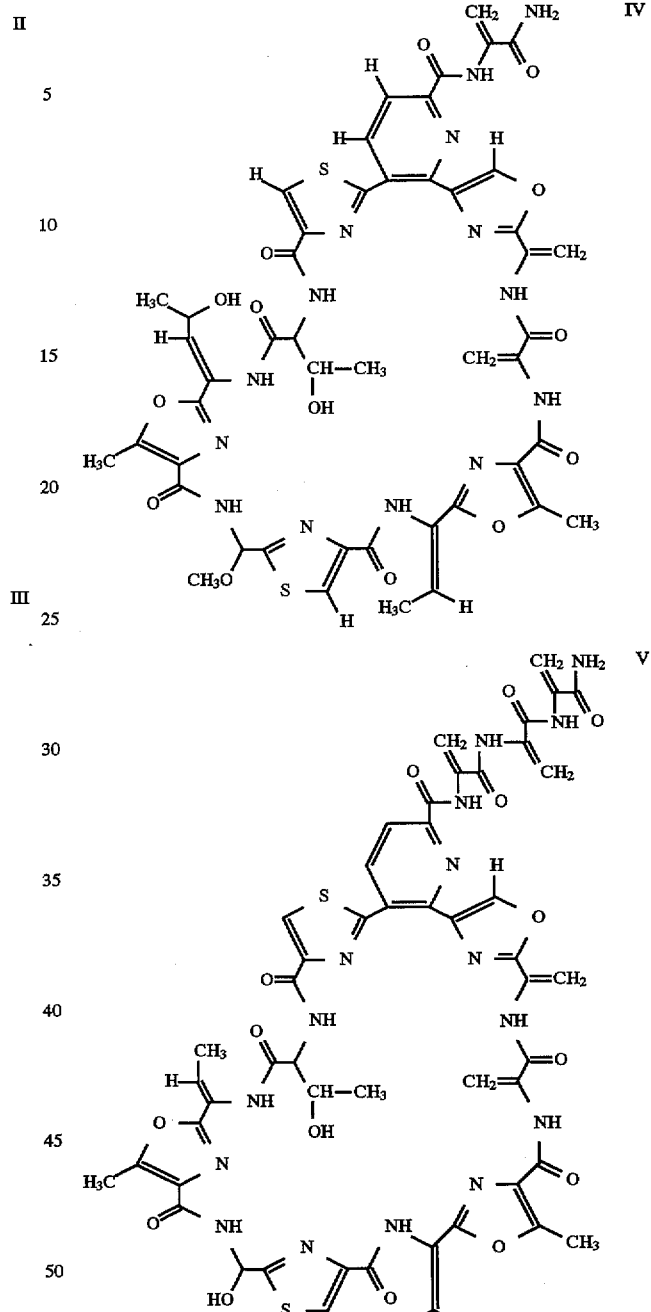
IV
V

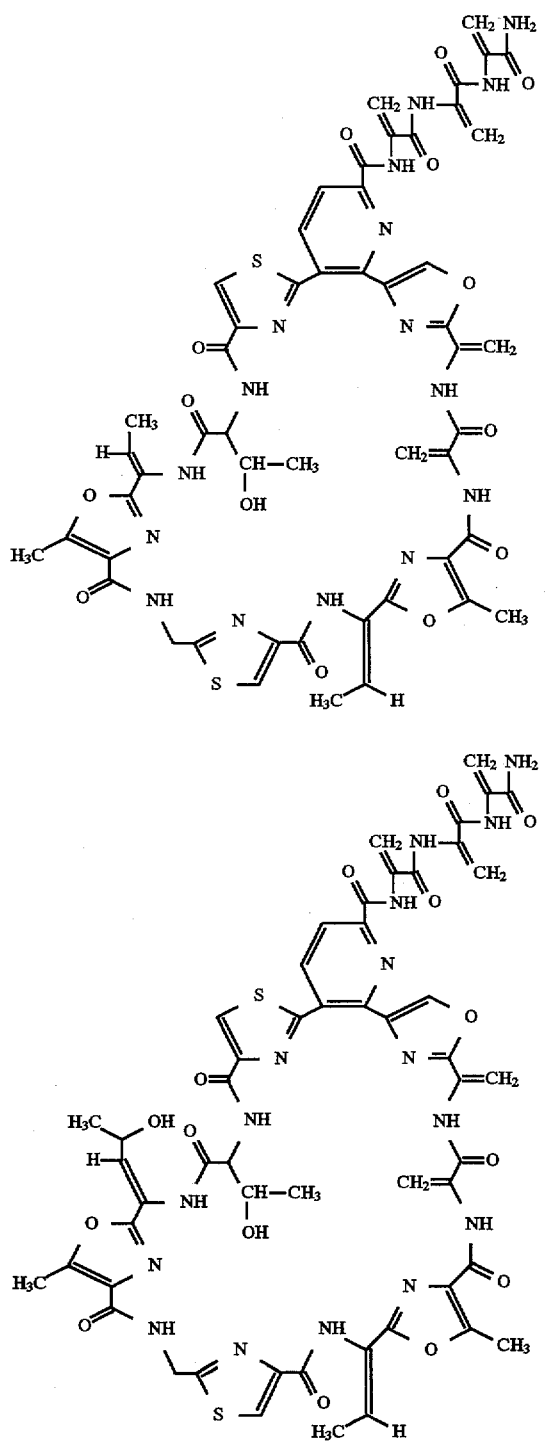

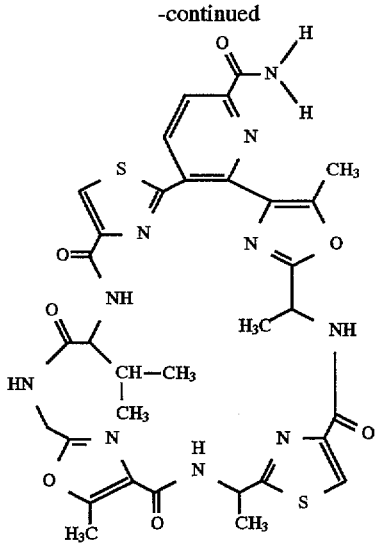

or pharmaceutically acceptable salts thereof.

2. The compound of formula I, II, III, IV, V, VI, VII, or IX of claim 1, except as existing or occurring in nature.

3. The compound of formula I, II, III, IV, V, VI, VII, or IX of claim 2 in essentially pure form.

4. The compound of formula IV of claim 1 which is 52-de[1-[[[1-(aminocarbonyl)ethenyl]amino]carbonyl]ethenyl]-sulfomycin I.

5. A feed composition, which comprises animal feed and an amount effective to promote growth of a compound of the formula I, II, III, IV, V, VI, VII, or IX of claim 1, or any combination thereof.

6. An animal premix which comprises an amount effective to promote growth of a compound of the formula I, II, III, IV, V, VI, VII, or IX of claim 1, or any combination thereof, and a suitable inert carrier therefor.

7. A method for promoting growth in animals which comprises administering to the animals an effective amount of a compound of the formula I, II, III, IV, V, VI, VII, or IX of claim 1, or any combination thereof.

8. The method of claim 7 wherein the animals are selected from the group consisting of poultry, sheep, cattle, and swine.

9. The method of claim 8 wherein the animals are chickens.

10. The method of claim 9 wherein the compound is administered orally in an amount of about 0.5 to about 11 mg/kg of feed.

11. The method of claim 8 wherein the animals are swine.

12. The method of claim 11 wherein the compound is administered orally in an amount of about 1 to about 55 mg/kg of feed.

* * * * *